(12) United States Patent
Leblanc et al.

(10) Patent No.: US 9,272,020 B2
(45) Date of Patent: Mar. 1, 2016

(54) IFN-BETA COMPOSITIONS, PREPARATION METHODS AND USES THEREOF

(75) Inventors: Daniel Leblanc, Geneva (CH); Evert Nicolaas Lamme, Nyon (CH); Helen Gabriela Baldascini, Rome (IT); Joel Richard, Mere (FR); Frederic Checot, Taluyers (FR); You-Ping Chan, Ternay (FR); Roger Kravtzoff, Algans (FR); Gauthier Pouliquen, Ternay (FR)

(73) Assignee: ARES TRADING S.A., Aubonne (CH)

( * ) Notice: Subject to any disclaimer, the term of this patent is extended or adjusted under 35 U.S.C. 154(b) by 42 days.

(21) Appl. No.: 14/118,757

(22) PCT Filed: May 16, 2012

(86) PCT No.: PCT/EP2012/059086
§ 371 (c)(1),
(2), (4) Date: Nov. 19, 2013

(87) PCT Pub. No.: WO2012/159945
PCT Pub. Date: Nov. 29, 2012

(65) Prior Publication Data
US 2014/0105858 A1      Apr. 17, 2014

Related U.S. Application Data

(60) Provisional application No. 61/488,544, filed on May 20, 2011.

(30) Foreign Application Priority Data

May 20, 2011   (EP) ..................................... 11305617

(51) Int. Cl.
  *A61K 38/21*   (2006.01)
  *A61K 9/00*    (2006.01)
  *A61K 47/34*   (2006.01)
  *A61K 47/36*   (2006.01)
  *A61K 9/20*    (2006.01)
  *A61K 9/19*    (2006.01)
  *A61K 47/42*   (2006.01)

(52) U.S. Cl.
  CPC ............. *A61K 38/215* (2013.01); *A61K 9/0019* (2013.01); *A61K 9/19* (2013.01); *A61K 9/2018* (2013.01); *A61K 47/34* (2013.01); *A61K 47/42* (2013.01)

(58) Field of Classification Search
  None
  See application file for complete search history.

(56) References Cited

U.S. PATENT DOCUMENTS

| 7,655,254 B2 * | 2/2010 | Dennis et al. ................. 424/422 |
| 2006/0099264 A1 | 5/2006 | Chan et al. |
| 2007/0289517 A1 | 11/2007 | Pouliquen et al. |
| 2009/0011028 A1 | 1/2009 | Checot et al. |
| 2009/0012028 A1 | 1/2009 | Chan et al. |

FOREIGN PATENT DOCUMENTS

| FR | 2840614 | 12/2003 |
| FR | 2862541 | 5/2005 |
| FR | 2915748 | 11/2008 |
| WO | WO 2008/135562 | 11/2008 |

OTHER PUBLICATIONS

Kricheldorf, H. R. "α-Aminoacid-N-Carboxy-Anhydrides and Related Heterocycles" *Springer-Verlag Berlin Heidelberg*, 1987, pp. 1-6.
Wang, W. "Instability, stabilization, and formulation of liquid protein pharmaceuticals" *International Journal of Pharmaceuticals*, 1999, pp. 129-188, Vo. 185.
Derynck, R. et al. "Isolation and structure of a human fibroblast interferon gene" *Nature*, Jun. 19, 1980, vol. 285.
Familletti, P. C. et al. "A Convenient and Rapid Cytopathic Effect Inhibition Assay for Interferon" *Methods in Enzymology*, 1981, pp. 387-394, vol. 78.
Mark, D. F. et al. "Site-specific mutagenesis of the human fibroblast interferon gene" *Proc. Natl. Acad. Sci. USA*, Sep. 1984, pp. 5662-5666, vol. 81.
Pestka S. "Interferon Standards and General Abbreviations" *Methods in Enzymology*, 1986, pp. 14-23, vol. 119.
Rubinstein, S. et al, "Convenient Assay for Interferons" *Journal of Virology*, Feb. 1981. pp. 755-758, vol. 37, No. 2.
Shepard. H. M. et al. "A single amino acid change in IFM-$\beta_1$ abolishes its antiviral activity" *Nature*, Dec. 10, 1981, vol. 294.
Wang, Y. et al. "Parental Formulations of Proteins and Peptides: Stability and Stabilizers" *Journal of Parental Science & Technology*, 1988, pp. S4-S26, vol. 42.

* cited by examiner

*Primary Examiner* — Christine J Saoud
*Assistant Examiner* — Jegatheesan Seharaseyon
(74) *Attorney, Agent, or Firm* — Saliwanchik, Lloyd & Eisenschenk

(57) ABSTRACT

The present invention pertains to interferon-beta (IFN-beta) compositions comprising interferon-beta and a grafted poly (glutamic acid) polymer having an average molecular weight between 26,000 and 40,000 g/mol, grafted with alpha-tocopherol substituents, the average molar grafting ratio being 4.5-5.5 moles %, the weight/weight ratio between said grafted poly(glutamic acid) polymer and IFN-beta being between 24 and 125. The present invention also pertains to the preparation methods of such compositions and their application to obtain therapeutic compositions in dosage unit form delivering IFN-beta over an extended period of time.

10 Claims, 1 Drawing Sheet

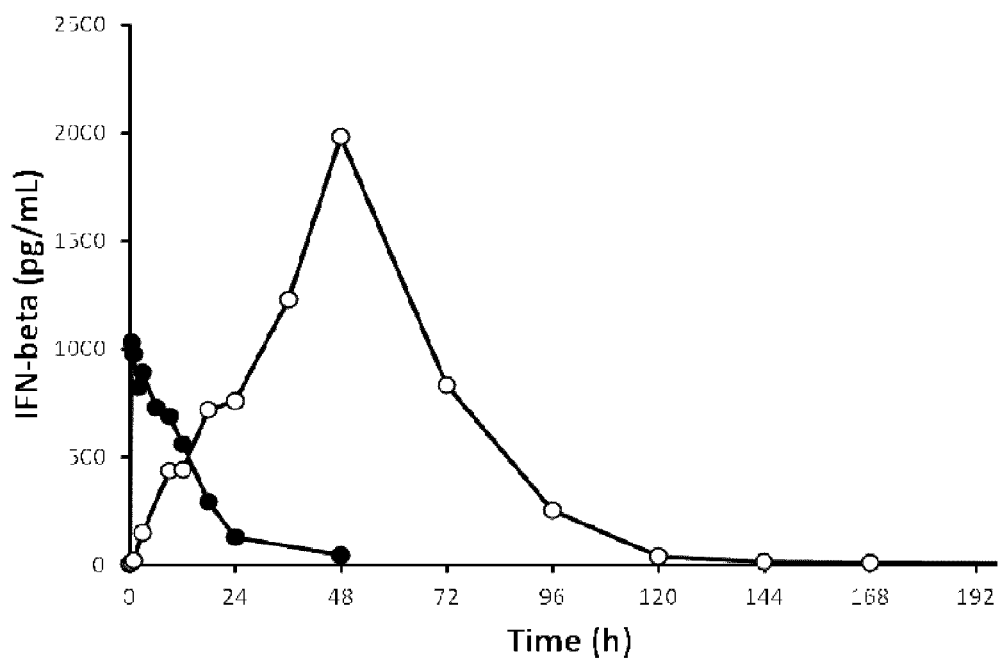

IFN-BETA COMPOSITIONS, PREPARATION METHODS AND USES THEREOF

CROSS-REFERENCE TO RELATED APPLICATIONS

This application is the U.S. national stage application of International Patent Application No. PCT/EP2012/059086, filed May 16, 2012, which claims the benefit of U.S. Provisional Patent Application No. 61/488,544, filed May 20, 2011.

FIELD OF THE INVENTION

The present invention relates to interferon-beta (IFN-beta) compositions, their preparation methods and application of these to obtain therapeutic compositions in dosage unit form delivering IFN-beta over an extended period of time.

Background on Interferons and their Stabilization

Interferons are cytokines, i.e. soluble proteins that transmit messages between cells and play an essential role in the immune system by helping to destroy microorganisms that cause infection and repairing any resulting damage. Interferons are naturally secreted by infected cells and were first identified in 1957. Their name is derived from the fact that they "interfere" with viral replication and production.

Interferons exhibit both antiviral and antiproliferative activity. On the basis of biochemical and immunological properties, the naturally-occurring human interferons are grouped into three major classes: interferon-alpha, interferon-beta and interferon-gamma Further, interferons (IFNs) are glycoproteins produced by the body in response to a viral infection. They inhibit the multiplication of viruses in protected cells. Consisting of a lower molecular weight protein, IFNs are remarkably non-specific in their action, i.e. IFN induced by one virus is effective against a broad range of other viruses. They are however species-specific, i.e. IFN produced by one species will only stimulate antiviral activity in cells of the same or a closely related species. IFNs were the first group of cytokines to be exploited for their potential anti-tumor and antiviral activities.

The three major IFNs are referred to as IFN-$\alpha$, IFN-$\beta$ and IFN-$\gamma$. Such main kinds of IFNs were initially classified according to their cells of origin (leukocyte, fibroblast or T cell). However, it became clear that several types might be produced by one cell. Hence leukocyte IFN is now called IFN-$\alpha$, fibroblast IFN is IFN-$\beta$ and T cell IFN is IFN-$\gamma$. There is also a fourth type of IFN, lymphoblastoid IFN, produced in the "Namalwa" cell line (derived from Burkitt's lymphoma), which seems to produce a mixture of both leukocyte and fibroblast IFN.

Every class of IFN contains several distinct types. IFN-$\beta$ and IFN-$\gamma$ are each the product of a single gene.

Human fibroblast interferon (IFN-$\beta$ or IFN-beta) has antiviral activity and can also stimulate natural killer cells against neoplastic cells. It is a polypeptide of about 20,000 Da induced by viruses and double-stranded RNAs. From the nucleotide sequence of the gene for fibroblast interferon, cloned by recombinant DNA technology, Derynk et al. (1980) deduced the complete amino acid sequence of the protein. It is 166 amino acids long.

Shepard et al. (1981) described a mutation at base 842 (Cys→Tyr at position 141) that abolished its antiviral activity, and a variant clone with a deletion of nucleotides 1119-1121.

Mark et al. (1984) inserted an artificial mutation by replacing base 469 (T) with (A) causing an amino acid switch from Cys→Ser at position 17. The resulting IFN-beta was reported to be as active as the 'native' IFN-beta and stable during long-term storage (−70° C.).

REBIF (Merck Serono) is interferon beta-1a, produced from mammalian cell lines. Its recommended International Non-proprietary Name (INN) is "interferon beta-1a".

The interferon unit or International Unit for interferon (U or IU) is defined as the amount necessary to protect 50% of the cells against viral damage; the assay that may be used to measure bioactivity is the cytopathic effect inhibition assay as first described by Rubinstein, et al., 1981 and Familletti, P. C., et al., 1981. In this antiviral assay for interferon, about 1 unit/mL of interferon is the concentration necessary to produce a cytopathic effect inhibition of 50%. The units for IFN-beta are determined with respect to the international reference standard for Hu-IFN-beta provided by the National Institutes of Health (Pestka, S. 1986).

The interferon unit or International Unit for interferon (U or IU) is defined as the amount necessary to protect 50% of the cells against viral damage; the assay that may be used to measure bioactivity is the cytopathic effect inhibition assay as first described by Rubinstein, et al., 1981 and Familletti, P. C., et al., 1981. In this antiviral assay for interferon, about 1 unit/mL of interferon is the concentration necessary to produce a cytopathic effect of 50%. The units for IFN-beta are determined with respect to the international reference standard for Hu-IFN-beta provided by the National Institutes of Health (Pestka, S. 1986).

As with all protein-based pharmaceuticals, one major obstacle that must be overcome in the use of IFN-beta as a therapeutic agent is the loss of pharmaceutical utility that can result from its instability in pharmaceutical compositions.

Physical instabilities that threaten protein activity and efficacy in pharmaceutical compositions include denaturation and formation of soluble and insoluble aggregates, while chemical instabilities include hydrolysis, imide formation, oxidation, racemization, and deamidation. Some of these changes are known to lead to the loss or reduction of the pharmaceutical activity of the protein of interest. In other cases, the precise effects of these changes are unknown, but the resulting degradative products are still considered to be pharmaceutically unacceptable due to the potential for undesirable side effects.

The stabilization of proteins in pharmaceutical compositions remains an area in which trial and error plays a major role (reviewed by Wang (1999) Int. J. Pharm. 185:129-188; Wang and Hanson (1988) J. Parenteral Sci. Tech. 42:S3-S26). Excipients that are added to protein pharmaceutical compositions to increase their stability include buffers, sugars, surfactants, amino acids, polyethylene glycols, and polymers, but the stabilizing effects of these chemical additives vary depending on the protein.

There is a need for improved IFN-beta pharmaceutical compositions comprising physiologically compatible stabilizers that improve the solubility of this protein and stabilize the protein against aggregate formation, thereby enhancing its pharmaceutical utility.

Despite the major efforts that have been applied to the problem, no completely satisfactory IFN-beta pharmaceutical compositions have yet been produced.

Therapeutic dosage unit forms have now been discovered which are easy to prepare, provide sustained release of IFN-beta and are available in solid or liquid form.

The Invention

It is an object of the present invention to provide a sustained-release composition of interferon-beta suitable for a once-a-week administration.

It is another object of the present invention to provide a sustained-release composition of IFN-beta which releases 60% of the IFN-beta over more than 120 min, preferably more than 180 min, using an in-vitro test T1 or 60% of the IFN-beta over more than 60 min, preferably more than 90 min, using an in-vitro test T2 described below.

It is another object of the present invention to provide a solid composition which is stable vis-à-vis the aggregation of IFN-beta, as the percentage of aggregates is lower than 20%, preferably lower than 10% and more preferably lower than 5% of the total amount of IFN-beta after two years of storage at 5° C. and after 6 months at 25° C.

It is another object of the present invention to provide an easy-to-inject liquid composition having a viscosity less than 1000 mPa·s, as measured at 20° C. and at a shear rate of $10\,s^{-1}$, using an AR1000 Rheometer (TA Instruments) or an equivalent apparatus with a cone-plate geometry, and a cone of 4 cm and 2° angle.

It has been noted surprisingly and unexpectedly that the combination of IFN-beta with specific grafted poly(glutamic acid) polymers allows providing easy-to-inject sustained-release compositions of IFN-beta, with improved stability evidenced by a low amount of formed aggregates.

The present invention thus relates to a solid pharmaceutical composition comprising:
interferon-beta (IFN-beta) and
a grafted poly(glutamic acid) polymer having an average molecular weight between 26,000 and 40,000 g/mol, in particular between 28,000 and 38,000 g/mol, and more particularly about 33,000 g/mol grafted with alpha-tocopherol substituents, the average molar grafting ratio being 4.5-5.5 moles %, wherein the weight/weight ratio between said grafted poly(glutamic acid) polymer and IFN-beta is between 24 and 125.

The present invention further relates to a liquid aqueous composition comprising:
IFN-beta and
a grafted poly(glutamic acid) polymer having an average molecular weight between 26,000 and 40,000 g/mol, in particular between 28,000 and 38,000 g/mol, and more particularly about 33,000 g/mol grafted with alpha-tocopherol substituents, the average molar grafting ratio being 4.5-5.5 moles %, wherein the weight/weight ratio between said grafted poly(glutamic acid) polymer and IFN-beta is between 24 and 125.

The present invention also relates to a method for preparing a solid composition comprising IFN-beta and a grafted poly(glutamic acid) polymer according to the invention.

The invention also relates to the above liquid or solid compositions for use in a method for therapeutic treatment of the human or animal body, particularly for use in a method of therapeutic treatment of chronic autoimmune central nervous system diseases or of neurodegenerative diseases, particularly of multiple sclerosis or of clinically isolated syndrome.

The invention also relates to the use of compositions for manufacturing a drug for the treatment of autoimmune central nervous system diseases or of neurodegenerative diseases, particularly multiple sclerosis or clinically isolated syndrome.

Definition of the Term Interferon Beta

The term "interferon beta" (IFN-beta or IFN-β), as used herein, is intended to include fibroblast interferon in particular of human origin, as obtained by isolation from biological fluids or as obtained by DNA recombinant techniques from prokaryotic or eukaryotic host cells, as well as its muteins, salts, functional derivatives, variants, analogs and active fragments.

As used herein the term "muteins" refers to analogs of IFN-beta in which one or more amino acid residues of a natural IFN-beta are replaced by different amino acid residues, or are deleted, or one or more amino acid residues are added to the natural sequence of IFN-beta, without changing substantially the activity of the resulting products as compared to the wild type IFN-beta. These muteins are prepared by known synthesis and/or by site-directed mutagenesis techniques, or any other known technique suitable therefor. Preferred muteins include e.g. the ones described by Shepard et al. (1981) or Mark et al. (1984).

Any such mutein preferably has an amino acid sequence sufficiently duplicative of the IFN-beta sequence to have substantially a similar or even a better activity than an IFN-beta. The biological function of interferon is well known to the person skilled in the art, and biological standards are established and available e.g. from the National Institute for Biological Standards and Control (See Worldwide Website: immunology.org/links/NIBSC).

Bioassays for the determination of IFN activity have been described. An IFN assay may for example be carried out as described by Rubinstein et al., 1981. Thus, it can be determined whether any given mutein has substantially a similar, or even a better, activity than IFN by means of routine experimentation.

Muteins of IFN-beta, which can be used in accordance with the present invention, or nucleic acid coding therefor, include a finite set of substantially corresponding sequences as substitution peptides or polynucleotides which can be routinely obtained by one of ordinary skill in the art, without undue experimentation, based on the teaching and guidance presented herein.

Preferred changes for muteins in accordance with the present invention are so-called "conservative" substitutions. Conservative amino acid substitutions of polypeptides or proteins of the invention may include synonymous amino acids within a group, which have sufficiently similar physico-chemical properties that substitution between members of the group will preserve the biological function of the molecule. It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the purview of the present invention.

Preferably, the synonymous amino acid groups are those defined in Table I hereunder. More preferably, the synonymous amino acid groups are those defined in Table II, and most preferably, the synonymous amino acid groups are those defined in Table III.

TABLE I

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |

TABLE I-continued

Preferred Groups of Synonymous Amino Acids

| Amino Acid | Synonymous Group |
|---|---|
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE II

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE III

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of IFN-beta for use in the present invention include any known method steps, such as presented in U.S. Pat. Nos. 4,959,314, 4,588,585 and 4,737,462, to Mark et al; U.S. Pat. No. 5,116,943 to Koths et al; U.S. Pat. No. 4,965,195 to Namen et al; U.S. Pat. No. 4,879,111 to Chong et al; and U.S. Pat. No. 5,017,691 to Lee et al, and lysine substituted proteins presented in U.S. Pat. No. 4,904,584 (Shaw et al). Specific muteins of IFN-beta have been described, for example by Mark et al., 1984.

The term “fused protein” refers to a polypeptide comprising an IFN-beta, or a mutein thereof, fused to another protein, which, e.g., has an extended residence time in body fluids. An IFN-beta may thus be fused to another protein, polypeptide or the like, e.g., an immunoglobulin or a fragment thereof.

“Functional derivatives” as used herein cover derivatives of IFN-beta, and their muteins and fused proteins, which may be prepared from the functional groups which occur as side chains on the residues or the N- or C-terminal groups, by means known in the art, and are included in the invention as long as they remain pharmaceutically acceptable, i.e. they do not destroy the activity of the protein which is substantially similar to the activity of IFN-beta, and do not confer toxic properties on compositions containing it. These derivatives may, for example, include polyethylene glycol side-chains, which may mask antigenic sites and extend the residence of IFN-beta in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties.

As “active fractions” of IFN-beta, or muteins and fused proteins, the present invention covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has no significantly reduced activity as compared to the corresponding IFN-beta.

The term “salts” of IFN-beta herein refers to salts of carboxyl groups and to salts of amino groups of the proteins described above or analogs thereof. Salts of a carboxyl group may be formed by means known in the art and include inorganic salts, for example, sodium, calcium, ammonium, ferric or zinc salts, and the like, and salts with organic bases such as those formed, for example, with amines, such as triethanolamine, arginine or lysine, piperidine, procaine and the like. Amine salts include, for example, mineral acids salts, such as hydrochloric acid salts or sulfuric acid salts, and organic acids salts, such as acetic acid salts or oxalic acid salts. Of course, any such salts must retain the biological activity of the proteins (IFN-beta) relevant to the present invention, i.e., the ability to bind to the corresponding receptor and initiate receptor signaling.

In accordance with the present invention, the use of recombinant human IFN-beta as the active ingredient of the invention is particularly preferred.

In accordance with the present application, the use of interferon beta-1a is particularly preferred.

Definition of the Grafted Poly(Glutamic Acid) Polymer

The grafted poly(glutamic acid) polymer according to the invention has a linear main chain, or backbone, consisting of alpha-glutamic acid units, corresponding to the structure (i) below:

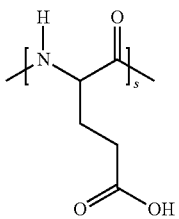

(i)

It may have L, D, or racemic (D,L)-configuration.

The grafted poly(glutamic acid) polymer according to the invention carries alpha-tocopherol groups linked by an ester bond to some of the pendant carboxylic groups.

According to a particular embodiment, the distribution of alpha-tocopherol grafted glutamate units is of random type.

"Random type" means that the alpha-tocopherol grafted glutamic units are distributed unevenly among the poly (glutamic acid) chain.

Unless otherwise specified, the term "glutamic" refers either to "glutamic acid" or "glutamate" throughout the description.

Alpha-tocopherol may be D-alpha-tocopherol (natural form), L-alpha-tocopherol or D,L-alpha-tocopherol (all racemic, synthetic).

The alpha-tocopherol of the invention can be natural or synthetic. Preferably, the alpha-tocopherol used in the invention is synthetic.

According to a particularly preferred embodiment, the grafted poly(glutamic acid) polymer does not include other grafts than alpha-tocopherol grafts.

In an aqueous medium, the residual (not grafted) carboxylic functions of the grafted poly(glutamic acid) polymer are either neutral (—COOH form) or ionized (—COO⁻ anion), depending on pH and composition. The neutrality of the grafted polymer thus requires the presence of a counter-cation, for example an inorganic monovalent cation such as sodium.

Thus, in aqueous solution, typically at pH 6 to 8, the grafted polymer is mainly in the form of grafted poly(glutamate).

The grafted poly(glutamic acid) polymers of the invention have the formula (I) below:

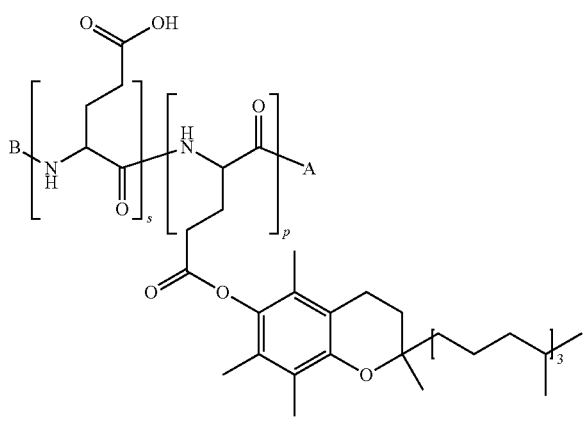

(I)

wherein
A represents:
a —NHR group wherein R represents a hydrogen, a linear C2 to C10, a branched C3 to C6 alkyl group or a benzyl group, or
a N-bound terminal amino acid unit;
B represents a hydrogen, a linear C2 to C6 acyl group, a branched C3 to C10 acyl group, or a pyroglutamate;
p corresponds to the average number of glutamic monomers carrying an alpha-tocopherol substituent;
s corresponds to the average number of non-grafted glutamic monomers.

The grafting ratio is defined as the average molar ratio $p/(s+p)$ of tocopherol substituents to glutamic units. The ratio $p/(s+p)$ is between 4.5 and 5.5%, preferably about 5%.

The average degree of polymerization $DP=s+p$ is between 180 and 250, preferably between 200 and 240, in particular about 220.

The grafted poly(glutamic acid) polymers of the invention can be obtained by methods known to those skilled in the art. They may be obtained using at least the methods described in patent application WO 03/104303, and in particular the method below.

Poly(alpha-glutamic acid) polymers are commercially available, such as those marketed by SIGMA-ALDRICH under ref. 386847. They can also be synthesized by polymerization of N-carboxyamino acid anhydrides (NCA), described, for example, in the article "Biopolymers, 1976, 15, 1869" and in the book by H. R. Kricheldorf "alpha-Aminoacid-N-carboxy Anhydride and related Heterocycles", Springer Verlag (1987). Reference can also be made to the patent FR 2 801 226.

The coupling of alpha-tocopherol with some of the carboxylic functions of the poly(glutamic acid) polymer is readily performed by reacting said polymer with alpha-tocopherol in the presence of a coupling agent and a catalyst in a suitable solvent such as dimethylformamide (DMF), N-methylpyrrolidone (NMP) or dimethyl sulfoxide (DMSO). The degree of grafting is controlled chemically via the stoichiometry of the constituents and reagents, or the reaction time.

Determination of the Grafted Poly(Glutamic Acid) Polymer Mass, Average Molar Grafting Ratio and Degree of Polymerization The average molecular weight is defined by Mp (peak molecular weight) measured by size exclusion chromatography.

To measure the average molecular weight, the polymer sample is precipitated by acidification with hydrochloric acid 0.1N, freeze-dried, then dissolved in NMP for analysis.

The absolute average peak molecular weight is measured by way of a size exclusion chromatography comprising three sequential polystyrene-co-divinylbenzene columns (5 µm/100 000 Å, 5 µm/10 000 Å and 5 µm/1 000 Å). This device is connected to an 18-angle light scattering detector (e.g. DAWN EOS—Wyatt Technology) and to a differential refractometer (e.g. OptiLab REX—Wyatt Technology).

The average molar alpha-tocopherol grafting ratio in the grafted poly(glutamic acid) polymer corresponds to the difference between the measured total alpha-tocopherol ratio and the measured free alpha-tocopherol ratio. The total alpha-tocopherol ratio is determined by $^1$H NMR, while the free alpha-tocopherol ratio is determined by HPLC.

The determination of the total alpha-tocopherol ratio is performed by $^1$H NMR with a spectrophotometer (Avance 300) equipped with QNP probe. The polymer sample is freeze-dried, then dissolved in deuterated trifluoroacetic acid for analysis.

Two signals are considered:
the massif around 0.6 ppm corresponds to the protons of the four methyl groups of the alpha-tocopherol aliphatic chain (12 protons), and
the massif around 4.5-4.7 ppm corresponds to the proton in α-position of the glutamic acid unit.

Each signal is integrated and the integral value corresponding to the proton in α-position of the glutamic acid unit is calibrated to 100.

A is considered the integral value obtained for the signal corresponding to the protons of the four methyl groups of the alpha-tocopherol aliphatic chain. The total alpha-tocopherol ratio is then given by the equation: % alpha-tocopherol=A/12.

The determination of the free alpha-tocopherol ratio is performed by HPLC by means of a microBondapak C18 column (300 mm long, 3.9 mm in internal diameter, filled with 10 micron diameter spherical silica) provided by Waters or similar, conditioned at 40° C. and eluted in isocratic mode with the mobile phase, comprising 25% vol methanol and 75% vol acetonitrile with a 1 mL/min flow rate.

The molar fraction $x_p$ in monomer units grafted with alpha-tocopherol groups, which corresponds to the average molar grafting rate in alpha-tocopherol groups, is determined this way.

The average degree of polymerization DP is calculated by dividing the average molecular weight of a polymer chain determined by size exclusion chromatography as described above, by the average molecular weight M of a monomer unit of the polymer: $DP=M_p/M$ This average molecular weight of a unit is the average of the molecular weights of the units constituting the polymer, each being weighted by the molar fraction of this unit.

Considering $M_1$ is considered the average molecular weight of the glutamic acid monomers, and $M_2$ the average molecular weight of glutamic acid monomers grafted with alpha-tocopherol. The average weight M is given by the following formula:

$$M=x_1 \cdot M_1 + x_2 \cdot M_2$$

Antioxidant

According to a particular embodiment, the IFN-beta solid composition or the IFN-beta aqueous solution further comprises an antioxidant.

The antioxidant is for example methionine, cysteine, ascorbic acid, an ascorbate, citric acid or a citrate. A preferred composition of the invention includes one or more different antioxidants.

The antioxidant of the invention is preferably methionine. Methionine used in the invention is particularly L-methionine.

In particular, a composition of the invention comprises an antioxidant in an antioxidant/IFN-beta weight/weight ratio between 2 and 7.

Lyoprotectant

According to a particular embodiment of the invention, an IFN-beta solid composition or an IFN-beta liquid aqueous composition further comprises a lyoprotectant.

The lyoprotectant is preferably a sugar. A preferred composition of the invention comprises one or several different sugars. "Sugar" means simple sugars (monosaccharides) or complex sugars (chains composed of several sugar units such as diholosides), but also, by extension, polyols.

Examples of lyoprotectants include lactose, glucose, fructose, and sucrose. Suitable polyols are for example mannitol, xylitol, erythritol, sorbitol, trehalose, maltodextrin, and mixtures thereof. Mannitol or sucrose, preferably the latter, are preferred lyoprotectants.

Examples of mannitol include various grades of PEARLITOL commercialized by Roquette, especially PEARLITOL, SD200.

According to a preferred embodiment, a composition of the invention, particularly a composition of the invention comprising an antioxidant as defined above, comprises between 50 and 600 mg of lyoprotectant per mg of IFN-beta.

A ready-to-use aqueous IFN-beta solution advantageously contains methionine in an amount of 2 to 7 mg per mg of IFN-beta and sucrose in a concentration from 50 to 300 mg/mL.

A composition of the invention containing an antioxidant and a lyoprotectant in aqueous solution advantageously has a pH of 6 to 8, preferably about 7.

Osmolality and pH Adjustment Additives

Additives which may be used for the composition osmolality adjustment include for example sodium chloride, potassium chloride, lactose, glucose, fructose, sucrose, mannitol, xylitol, erythritol, sorbitol, trehalose, maltodextrin, and mixtures thereof.

Additives used for the composition pH adjustment include for example a basic compound, especially a mineral base such as a hydroxide, particularly sodium hydroxide. Acetic acid or hydrochloric acid may also be used.

A particularly preferred solid composition contains the following ingredients in the proportions indicated:
a) about 0.5 mg IFN-beta;
b) about 22 mg of grafted poly(glutamic acid) polymer having an average molecular weight between 26,000 and 40,000 g/mol, grafted with alpha-tocopherol substituents, the average molar grafting ratio being 4.5-5.5 moles %;
c) about 1.5 mg methionine; and
d) about 76 mg sucrose;
or a multiple or sub-multiple of said amounts.

The above amounts may for example be multiplied by a value between 0.3 and 5, such as 0.3, 0.5, 1.2, 1.5, 2, 3, 5, or even more.

Another particularly preferred solid composition of the invention is a dehydrated composition, particularly a lyophilisate, i.e. a freeze-dried composition.

Preferably, the nature and amounts of the ingredients are selected such that the solid aqueous composition is stable at 5° C. for at least 24 months.

Manufacturing Method: IFN-Beta Solid Composition Comprising IFN-Beta and Grafted Poly(Glutamic Acid) Polymer The present invention particularly provides a method for preparing the solid composition of the invention, comprising the following steps:

(a) providing a grafted poly(glutamic acid) polymer liquid aqueous solution at a concentration between 20 and 30 mg/g;

(b) providing a solution of IFN-beta at a concentration between 1 and 9 mg/mL, wherein at least one compound, selected from a lyoprotectant, an antioxidant and an additive for pH adjustment, is present in at least one of the solutions of step (a) and step (b);

(c) mixing the solutions obtained in step (a) and (b), such that after mixing the composition:
has a polymer concentration between 4 and 16 mg/g,
has an osmolality between 100 and 250 mOsm/kg, and
has a pH between 6.5 and 7.5;

(d) sterilizing at least once the resulting mixture at least once; and (e) dehydrating the solution to form said solid composition.

More particularly, the present invention provides a method for preparing a solid composition, comprising the following steps:

(a) providing a grafted poly(glutamic acid) polymer liquid aqueous solution at a concentration between 20 and 30 mg/g;

(b) providing a solution of IFN-beta at a concentration between 1 and 9 mg/mL, preferably at a concentration of 6 mg/mL, wherein at least one compound, selected from a lyoprotectant, an antioxidant and an additive for pH adjustment, is present in at least one of the solutions of step (a) and step (b);

(c) mixing the solutions obtained in step (a) and (b), such that after mixing the composition:
has a polymer concentration between 7 and 13 mg/g,
has an osmolality between 100 and 160 mOsm/kg, and
has a pH between 6.8 and 7.2;

(d) sterilizing the resulting mixture at least once; and (e) dehydrating the solution to form said solid composition.

Even more particularly, the present invention provides a method for preparing a solid composition, comprising the following steps:

(a) providing a grafted poly(glutamic acid) polymer liquid aqueous solution at a concentration between 20 and 30 mg/g;

(b) providing a solution of IFN-beta of 6 mg/mL, wherein at least one compound, selected from a lyoprotectant, an antioxidant and an additive for pH adjustment, is present in at least one of the solutions of step (a) and step (b);

(c) mixing the solutions obtained in step (a) and (b), such that after mixing the composition:
has a polymer concentration of 9.7 mg/g,
has an osmolality of 136 mOsm/kg, and
has a pH of 7.0;

(d) sterilizing at least once the resulting mixture; and (e) dehydrating the solution to form said solid composition.

Preferably, the liquid composition of step (d) is stored at rest for 2 hrs or more, preferably for 4 hrs or more, at room temperature before dehydration.

According to a preferred method, steps (a) and (b) can be achieved in glass bottles, fitted with magnetic stirrers, and preferably in well-known scalable equipment such as well-stirred tanks and stirrers. Stirrers are selected among those inducing either axial or radial flows, preferably stirrers inducing minimum shear stress and more preferably the Mixel TT propeller.

According to a preferred embodiment, step (d) is performed by sterile filtering and comprises several filtration steps, preferably two steps spaced out by at least 2 hrs stirring at room temperature. In particular, 0.2 micron filters can be used, such as Supor EKV Filters fitted with polyethersulfone membranes from Pall.

The filtered solution obtained at step (d) is dehydrated at step (e) by any well-known dehydration technique such as freeze-drying, atomization or evaporation, preferably freeze-drying.

According to a particular embodiment, the solution is distributed into flasks or vials before the dehydration step (e).

According to another particular embodiment, the flasks or vials are filled with glass beads.

A solid composition according to the invention allows, by addition of a solvent such as water, the preparation of the corresponding liquid composition. In particular, it allows, for example by adding water for injection (WFI), the preparation of a liquid injectable ready-to-use composition.

Method for Preparing a Ready-to-Use Liquid Composition

The invention thus provides a method for preparing a ready-to-use liquid composition, comprising dissolving an above solid composition of IFN-beta and grafted poly (glutamic acid) polymer having an average molecular weight between 26,000 and 40,000 g/mol and randomly grafted with alpha-tocopherol substituents, wherein the molar average grafting ratio is between 4.5 and 5.5 moles %, said solid composition preferably containing an antioxidant and a lyoprotectant, in a volume of diluent such that the concentration of IFN-beta is between 0.2 and 0.8 mg/mL and the concentration of grafted poly(glutamic acid) polymer is between 19 and 25 mg/mL in the ready-to-use liquid composition.

The invention therefore also relates to a liquid aqueous composition comprising:
IFN-beta and
a grafted poly(glutamic acid) polymer having an average molecular weight between 26,000 and 40,000 g/mol, grafted with alpha-tocopherol substituents, the average molar grafting ratio being 4.5-5.5 moles %, wherein the weight/weight ratio between said grafted poly(glutamic acid) polymer and IFN-beta is between 24 and 125.

In a preferred liquid composition of the invention, the concentration of IFN-beta is between 0.2 and 0.8 mg/mL.

In another preferred liquid composition of the invention, the concentration of grafted poly(glutamic acid) polymer is from 19 to 25 mg/mL.

In a particularly preferred liquid composition of the invention, the concentration of IFN-beta is between 0.2 and 0.8 mg/mL and the concentration of grafted poly(glutamic acid) polymer is from 19 to 25 mg/mL.

Particularly preferred liquid compositions of the invention contain the following components:

a) about 0.5 mg/ml IFN-beta;
b) about 22 mg/ml of poly(glutamic acid) polymer having an average molecular weight between 26,000 and 40,000 g/mol, grafted with alpha-tocopherol substituents, the average molar grafting ratio being 4.5-5.5 moles %;
c) about 1.5 mg/ml methionine; and
d) about 76 mg/ml sucrose;
or a multiple or sub-multiple of said amounts.

This liquid aqueous composition preferably has a pH of about 7 and an osmolality of about 300 mOsm/kg.

Preferably, the nature and amounts of the ingredients are selected such that the liquid aqueous composition has a viscosity lower than 1000 mPa·s, as measured at 20° C. and at a shear rate of 10 s$^{-1}$.

MATERIALS AND METHODS

Determination of the Hydrogels' Size

The polymer used for the invention is able to form spontaneously highly hydrated nanometric hydrogels when dispersed in an aqueous medium, in particular in water, at a pH between 6 and 8. IFN-beta spontaneously associates with the hydrogels.

The hydrogels' volume-averaged mean hydrodynamic diameter is measured by dynamic light scattering according to well-known techniques, for example by means of a Malvern Zetasizer Nano ZS or an ALV CGS 3 equipment. In the latter case the scattering angle is 140°.

To achieve the measurement, the solid composition is dissolved in water to obtain a polymer concentration of 22 mg/ml. Then 0.15 M NaCl is added such that the polymer concentration is 1 mg/ml. The solution is gently stirred for 24 hrs, then filtered through two sequential filters of respectively 0.8 and 0.2 µm pore size before dynamic light scattering analysis at a pH between 6 and 7.

The acquisition time of the scattering signal is 10 minutes. The measurement is performed in triplicate on two solution samples. The result is the mean over the 6 measurements.

Preferably, according to the present invention, the hydrogels have a volume-averaged mean hydrodynamic diameter between 10 and 80 nm, preferably between 10 and 60 nm, and more preferably between 10 and 30 nm Assessment Method of the Aggregation of IFN-Beta A suitable composition according to the invention has a percentage of aggregates, measured with the Stress test (ST) below, lower than 20%, preferably lower than 10% and more preferably lower than 5% of the total amount of IFN-beta.

Two types of IFN-beta aggregates can be formed: irreversible aggregates that cannot be dissociated by surfactants, and reversible aggregates that are dissociated by surfactants.

The quantification of the irreversible aggregates is conveniently performed by a size exclusion chromatography (SEC) method in the presence of sodium dodecyl sulfate (SDS).

However, the SEC-SDS method extracts, but also dissociates, the reversible aggregates, for example non-covalent dimers of IFN-beta. Obviously this method is not applicable to the measurement of the reversible aggregates.

A second method referred to hereafter as "Western blot" method has been developed to quantify both types of aggregates of IFN-beta.

Stress Test (ST):

0.7 mL samples of the freshly-prepared compositions to be tested are placed in 3-mL vials and heated for 30 min at 90° C. The compositions are then analyzed either by SEC-SDS, or by Western blot as described below.

Measurement of the Irreversibly Aggregated Forms by SDS-SEC

The content in irreversible aggregates is assayed by comparison with a standard IFN-beta containing 1 to 1.5% irreversible aggregates. This standard consists of IFN-beta aggregated in aqueous solution at 100° C. for 3.5 min, then diluted in a solution of grafted poly(glutamic acid).

The standard and the samples are both diluted 20-fold in 2% SDS.

The samples are injected in a chromatographic system consisting of two columns connected in series, TSK-Gel G4000 PWXL+TSK-Gel SuperAW400. The mobile phase is a 3.3 mM PBS solution comprising 0.3% SDS.

When irreversible aggregates are not detected or are below the standard, the aggregate content of the composition is quoted below 2%.

When irreversible aggregate content is above the standard, the quantification of aggregates is estimated through the quantification of the non-aggregated IFN-beta (monomer).

Measurement of Both Irreversible and Reversible Aggregates by Western Blot

Stage 1:

100 ng of IFN-beta composition are diluted in Laemmli buffer at pH=6.8 (0.01% SDS, 62.4 mM Tris(hydroxymethyl) aminomethane buffer solution, 0.06% bromophenol blue, 10% glycerol) and deposited in wells containing a 12% polyacrylamide gel.

Three standard solutions comprising 1 ng, 3 ng and 5 ng of IFN-beta are mixed with grafted poly(glutamic acid) polymer in the same proportion as the samples to analyze.

The grafted poly(glutamic acid) polymer, the IFN-beta and the aggregates are then separated by polyacrylamide gel electrophoresis in the presence of SDS (SDS-PAGE). The running buffer is a <<XT MES Running buffer>> (Biorad—Ref 161 0789) containing between 1 and 2.5% SDS.

Stage 2:

After migration of the proteins in the gel, the different forms of IFN-beta (monomer and aggregates) are transferred onto a nitrocellulose membrane. IFN-beta is then specifically revealed using a primary anti-IFN-beta antibody, followed by a secondary antibody coupled to alkaline phosphatase. The membrane is then stained by a mixture of 5-bromo-4-chloro-3'-indolyphosphate, p-toluidine (BCIP) and nitro blue tetrazolium chloride (NBT) where IFN-beta is detected by the antibodies.

After staining, the aggregates of IFN-beta appear as well separated colored bands. The direct visual comparison of band intensities allows the determination of the aggregate content in the tested compositions.

Determination of the In-Vitro Release Profile of the Composition According to the Invention The compositions are injected into a porosity-controlled material through which runs a synthetic buffer containing 10 mM PBS, 2% SDS and 30 mg/mL BSA. Samples are collected at regular intervals (every 30 minutes for a composition of the invention and every 2 minutes for the composition not containing the poly(glutamic acid) polymer) with a fraction collector (FC204 from Gilson) and analyzed by ELISA dosage (FUJIREBIO ref. KAC1201) for the IFN-beta content.

Depending on the experiment, either version described hereinafter can be used.

In-Vitro Test T1

The in vitro release test is performed using a temperature-controlled flow-through apparatus (a flow cell from SOTAX—No. 3239—with a diameter of 22.6 mm) filled with 1 mm diameter glass beads from SOTAX—No. F200-0110 in its lower part. A constant mass of solution is injected in an inert and porosity-controlled material (30 mm height and 25 mm diameter piece of foam from Carpenter—No. RP30263) located in the upper part of the chamber of the apparatus. A synthetic buffer containing 10 mM PBS, 2% SDS and 30 mg/mL BSA runs through this chamber at a temperature of 37° C. and at a flow rate of 0.5 ml/min. 50 µL of the sample is injected in the inert and porosity-controlled material at a 0.5 cm depth using a 100 µl syringe fitted with a 50 mm needle. The syringe is weighed before and after injection so as to precisely determine the amount of solution injected.

Results are expressed as the percentage of IFN-beta released at each time point versus the total IFN-beta amount released over 16 hrs.

In-vitro test T2

The in vitro release test is performed using a temperature-controlled flow-through apparatus (a flow cell from SOTAX—No. 3239—with a diameter of 22.6 mm) fully filled with 1 mm diameter glass beads from SOTAX—No. F200-0110. A constant mass of solution is injected into the glass beads' bed (inert and porosity-controlled medium). A synthetic buffer containing 10 mM PBS, 2% SDS and 30 mg/mL BSA runs through this chamber at a temperature of 37° C. and at a flow rate of 0.5 ml/min. 50 µL of the sample is injected in the inert and porosity-controlled material at a 0.5 cm depth using a 100 µl syringe fitted with a 50 mm needle. The syringe is weighed before and after injection so as to precisely determine the amount of solution injected.

Results are expressed as the percentage of IFN-beta released at each time point versus the total IFN-beta amount released over 15 hrs.

The invention will now be described by means of the following figures, examples and experiments.

FIGURES

FIG. 1 represents the plasma concentration of IFN-beta released as a function of time, wherein:

⊖⊖ represents the plasma concentration of IFN-beta released from the liquid composition F, and ●● represents the plasma concentration of IFN-beta released from the immediate-release formulation.

PREPARATIONS

Preparation 1: Grafted Poly(Glutamic Acid) Polymer Having a Degree of Polymerization (DP) of about 220 Grafted with about 5 Mole % Alpha-Tocopherol (Polymer P1)

An aqueous solution of grafted poly(glutamic acid) polymer having a degree of polymerization (DP) of about 220 grafted with about 5 mole % alpha-tocopherol was prepared as follows:

15 g of poly(alpha-L-glutamic acid), having a DP of about 220, obtained by polymerizing NCAGluOMe followed by hydrolysis, were dissolved in 288 mL of dimethylformamide (DMF) and heated at 80° C. The solution was cooled to 15° C. and 2.5 g of racemic alpha-tocopherol (>98% obtained from FLUKA) dissolved in 8 mL of DMF, 280 mg of 4-dimethylaminopyridine dissolved in 1 mL DMF and 1.6 g of diisopropylcarbodiimide dissolved in 6 mL of DMF were added successively. After 3.5 h stirring, the reaction medium was neutralized with aqueous sodium hydroxide. The polymer was then purified by ultrafiltration using a 1 kDa membrane and concentrated to about 30 mg/mL. The solution was filtered through a 0.22 um membrane, and stored at 5° C. before use in the next step. The yield was of about 85% of polymer P1.

The absolute peak molecular weight (Mp) measured by an 18-angle light scattering detector (MALLS) connected to an organic size exclusion chromatography was found to be 31,000 g/mol. The alpha-tocopherol grafting ratio, estimated by proton NMR spectroscopy, was 5.1 moles %.

Preparation 2: IFN-Beta Solution

A diluted solution of IFN-beta in 50 mM acetate buffer (Merck Serono, Switzerland—0.377 mg/mL or 0.399 mg/mL depending on solution batches) was concentrated by frontal ultrafiltration at room temperature to yield an IFN-beta solution concentrated at 6 mg/mL.

Preparation 3: Excipients Solution 4.7 g of methionine, 229.3 g of sucrose, and 4.6 g of 1 N sodium hydroxide solution were dissolved in 1645.4 g of water for injection (WFI). The resulting solution was kept under moderate stirring for 15 min at room temperature.

Preparation 4: Preparation of a Liquid Aqueous Composition of Grafted Poly(Glutamic Acid) Polymer and IFN-Beta of the Invention 1526.0 g of the excipients solution obtained in Preparation 3 were added to 1974.0 g of polymer P1 solution (28.2 mg/mL polymer P1 solution) obtained by the method described in Preparation 1. This solution was gently stirred for at least 15 min at room temperature.

145 g of 6 mg/mL IFN-beta solution of Preparation 2 were added to 2409.4 g of the intermediate solution above. The resulting mixture was stirred at room temperature for at least 2 hrs before being sterilized by filtration using 0.2 μm filters.

Preparation 5: Preparation of a Liquid Aqueous Composition of Grafted Poly(Glutamic Acid) Polymer and IFN-Beta of the Invention Preparation 5 was prepared using a protocol similar to that described for Preparation 4, using 2227.8 g of polymer P1 solution and adjusting accordingly the amounts of excipients and IFN-beta to obtain at the end of this stage a solution having the same composition and pH as Preparation 4.

Preparation 6: Preparation of a Liquid Aqueous Composition of Grafted Poly(Glutamic Acid) Polymer and IFN-Beta of the Invention Preparation 6 was prepared using a protocol similar to that described for Preparation 4, using 1553.4 g of the solution of excipients obtained in Preparation 3, 1688.6 g of polymer P1 solution and 1450.1 g of water for injection (WFI).

177.9 g of 6 mg/mL IFN-beta solution of Preparation 2 were added to 4682.1 g of the intermediate solution above. The resulting mixture was stirred at room temperature for at least 2 hrs before being sterile filtered using 0.2 μm filters.

Preparation 7: Grafted Poly(Glutamic Acid) Polymer Having a Degree of Polymerization (DP) of about 100 Grafted with about 5 Mole % Alpha-Tocopherol (Polymer P2)

An aqueous solution of grafted poly(glutamic acid) polymer having a degree of polymerization (DP) of about 100 grafted with about 5 mole % alpha-tocopherol was prepared using a protocol similar to that described for Preparation 1 using a raw poly(glutamic acid) polymer having a degree of polymerization (DP) of about 100.

The peak molecular weight (Mp) was estimated to be about 15,000 g/mol. The alpha-tocopherol grafting ratio, estimated as described in the method above, was about 5 moles %.

Preparation 8: Preparation of a Liquid Aqueous Composition of Grafted Poly(Glutamic Acid) Polymer and IFN-Beta of the Invention Preparation 8 was prepared using a protocol similar to that described for Preparation 6, using 8.5 g of polymer P1 solution and adjusting accordingly the amounts of excipients and IFN-beta to obtain at the end of this stage a solution having the same composition and pH as Preparation 6.

Preparation 9: Preparation of a Liquid Aqueous Composition of Grafted Poly(Glutamic Acid) Polymer and IFN-Beta Out of the Scope of the Invention An excipients solution is prepared according to a protocol similar to that of Preparation 3 using 0.02 g of methionine, 0.96 g of sucrose and 9.01 g of water for injection (WFI). 8.42 g of the previous excipients solution were added to 9.66 g of water for injection (WFI) and to 7.31 g of polymer P2 solution (46.7 mg/mL polymer P2 solution) obtained by the method described in Preparation 7. This solution was gently stiffed for at least 15 min at room temperature.

0.96 g of 6 mg/mL IFN-beta solution of Preparation 2 was added to 25.33 g of the intermediate solution above. The resulting mixture was stirred at room temperature for at least 2 hrs.

EXAMPLES

Example 1

Preparation of a Solid Composition of Grafted Poly(Glutamic Acid) Polymer and IFN-Beta of the Invention The solution obtained in Preparation 4 was left to rest 16 h, then it was divided into 5 mL vials, each filled with 2.06 g of solution and 3 glass beads of diameter 4.76 mm It was then freeze-dried in a USIFROID lyophilizer (Model SMH-150) with a freeze-drying cycle for a total of 72 h, to produce a solid composition of the invention.

Example 2

Preparation of a Reconstituted Aqueous Composition of a Grafted Poly(Glutamic Acid) Polymer and IFN-Beta of the Invention 1.3 mL of water for injection were added per vial of freeze-dried product of Example 1 and stiffed manually for a few minutes to obtain a solution of the invention. Characteristics of this reconstituted solution are given in Experiment 1 below.

Example 3

Preparation of a Solid Composition of Grafted Poly(Glutamic Acid) Polymer and IFN-Beta of the Invention The solution obtained in Preparation 5 was left to rest 16 h, then it was divided into 5 mL vials, each filled with 2.06 g of solution and 3 glass beads of diameter 4.76 mm It was then freeze-dried in a USIFROID lyophilizer (Model SMH-150) with a freeze-drying cycle for a total of 72 h, to produce a solid composition of the invention.

Example 4

Preparation of a Reconstituted Aqueous Composition of a Grafted Poly(Glutamic Acid) Polymer and IFN-Beta of the Invention 1.3 mL of water for injection were added per vial of freeze-dried product of Example 3 and stirred manually for a few minutes to obtain a composition of the invention. Characteristics of this reconstituted solution are given in Experiment 1 below.

Example 5

Preparation of a Solid Composition of Grafted Poly(Glutamic Acid) Polymer and IFN-Beta of the Invention The end mixture of solution obtained in Preparation 6 is left to rest 2 hrs then it is divided into 5 ml vials, each filled with 3.08 g of solution and 3 glass beads of diameter 4.76 mm It is then freeze-dried in a USIFROID lyophilizer (Model SMH-150) with a freeze-drying cycle for a total of 96 h, to produce a solid composition of the invention.

Example 6

Preparation of a Reconstituted Aqueous Composition of a Grafted Poly(Glutamic Acid) Polymer and IFN-Beta of the Invention 1.3 ml of water p.p.i. for injection were added per vial of lyophilisate of Example 5 and stirred manually for a few minutes to obtain a reconstituted solution of the invention. Characteristics of this reconstituted solution are given in Experiment 1 below.

Example 7

Preparation of a Solid Composition of Grafted Poly(Glutamic Acid) Polymer and IFN-Beta of the Invention The end mixture of solution obtained in Preparation 8 is left to rest 2 hrs, then it is divided into 5 ml vials, each filled with 3.08 g of solution and 3 glass beads of diameter 4.76 mm.

It is then freeze-dried in a USIFROID lyophilizer (Model PL45) with a freeze-drying cycle for a total of 98 h, to produce a solid composition of the invention.

Example 8

Preparation of a Reconstituted Aqueous Composition of a Grafted Poly(Glutamic Acid) Polymer and IFN-Beta of the Invention 1.3 ml of water p.p.i. for injection were added per vial of lyophilisate of Example 7 and stirred manually for a few minutes to obtain a reconstituted solution of the invention of which the theoretical composition is given in table A below.

TABLE A

| Characteristics of the formulations of Example 8 of the invention | |
|---|---|
| Analysis | Example 8 |
| $C_{IFN\text{-}beta}$ (mg/mL) | 0.5 |
| $C_{Pol}$ (mg/mL) | 22 |

Example 9

Preparation of a Solid Composition of Grafted Poly(Glutamic Acid) Polymer and IFN-Beta Out of the Scope of the Invention The end mixture of solution obtained in Preparation 9 is left to rest 2 hrs then it is divided into 5 ml vials, each filled with 3.08 g of solution and 3 glass beads of diameter 4.76 mm It is then freeze-dried in a USIFROID lyophilizer (Model PL45) with a freeze-drying cycle for a total of 98 h, to produce a solid composition of the invention.

Example 10

Preparation of a Reconstituted Aqueous Composition of a Grafted Poly(Glutamic Acid) Polymer and IFN-Beta Out of the Scope of the Invention 1.3 ml of water p.p.i. for injection were added per vial of lyophilisate of Example 9 and stirred manually for a few minutes to obtain a reconstituted solution of the invention of which the theoretical composition is given in table B below.

TABLE B

Characteristics of the formulations of Example
10 out of the scope of the invention

| Analysis | Example 10 |
|---|---|
| $C_{IFN-beta}$ (mg/mL) | 0.5 |
| $C_{Pol}$ (mg/mL) | 30 |

EXPERIMENTATIONS

Experiment 1

Characterization of Liquid Aqueous Compositions of Examples 2, 4 and 6

IFN-Beta Concentration

The concentration of IFN-beta ($C_{IFN-beta}$) was measured by HPLC (reverse phase C4 column Symmetry300) with an elution gradient, with phases composed of water/acetonitrile+0.1% trifluoroacetic acid (TFA)+0.4 g/L polyoxyethylene(23) lauryl ether (phase A 70/30; Phase B 0/100). A preliminary extraction of the sample was made with a 6 g/L solution of bovine serum albumin according to a dilution factor of 3.

Quantification of IFN-beta in the compositions was performed versus a standard range of IFN-beta.

Polymer Concentration

A total acid hydrolysis of the sample was performed. The product was derivatized by ortho-phthalaldehyde and analyzed by reverse phase HPLC to determine the polymer concentration $C_{pol}$.

Osmolality

The osmolality of the composition was determined using a Fiske osmometer (MARK3).

The results obtained are given in Table 1:

TABLE 1

Characteristics of the formulations of
Examples 2, 4 and 6 of the invention

| Analysis | Example 2 | Example 4 | Example 6 |
|---|---|---|---|
| $C_{IFN-beta}$ (mg/mL) | 0.51 | 0.50 | 0.48 |
| $C_{Pol}$ (mg/mL) | 22 | 22 | 22 |
| pH | 6.9 | 6.9 | 7 |
| Osmolality (mOsm/kg) | 318 | 308 | 306 |
| Viscosity (mPa · s) | 48 | 53 | 21 |
| Particle Size (nm) | 18 | 17 | 17 |

Experiment 2

Antiviral Activity

The antiviral activity of IFN-beta was assessed by a test of inhibition of cytopathic effect; this test is based on the ability of IFN-beta to protect WISH cells (amniotic cells of human origin) from cytopathogenic action of VSV (vesicular stomatitis virus). Interpretation of the test is based on the fact that many viruses such as VSV lead to cell death that can be quantified indirectly by staining living cells. The cytopathic effect can therefore be used to quantify the protection by interferon. The indirect assessment of cell death is based on the measurement of viability, estimated by the amount of tetrazolium salts (MTT) that penetrates living cells. The method involves determining the percentage of protected cells with an automatic spectrophotometer and analysis according to the model of parallel lines in 3 points for statistical evaluation of the IFN-titer.

Protocol:

The test was performed in microtiter plates.

a. A small volume of culture medium (MEM/5% FBS) was added to each well.

b. In the plate, three successive dilutions (pitch of 1.5 from one row to another) were performed for the interferon-beta sample and the standard solution, so as to obtain three concentrations of interferon-beta (0.08 ng/mL, 0.12 ng/mL, 0.18 ng/mL) positioned in the linear dose-response curve.

c. A WISH cell suspension ($4 \times 10^4$ cells/well) was added to each well and the plates were incubated at 37° C. for 18-22 h in an incubator under 5% humidified $CO_2$.

d. A suspension of VSV was added to each well, except the control wells containing only MEM/2.5% FBS.

e. The plates were incubated at 37° C. for 20 to 28 h in an incubator under 5% humidified $CO_2$.

f. After verification by inverted microscope that:
 (1) in the row of positive virus control, at least 80% of cells died and
 (2) the average percentage of protection in the presence of the standard of IFN-beta is around 84% for the undiluted standard, 45% for dilution to 1/1.5, and 27% for dilution to 1/3, cultures are labeled with the specific MTT dye.

g. The intensity of the colour is determined by measuring the optical density (OD) at 595 nm using an automatic spectrophotometer.

h. To quantify the activity of IFN-beta, measurements of optical density (OD) are then analyzed using computer software (Colombo).

The results obtained are given in Table 2:

TABLE 2

Antiviral activity of the compositions
of Examples 2 and 4 of the invention

| | Example 2 | Example 4 |
|---|---|---|
| Antiviral activity in MIU/mL (% recovery) * | 125.4 (96) | 129.8 (101) |

* Percentage of recovery obtained versus the theoretical activity expected for the native protein at the same concentration in the same conditions of antiviral test.

These results evidence that the antiviral activity of the IFN-beta protein of the compositions of Examples 2 and 4 of the invention is 100% conserved.

Experiment 3

Evaluation of the Aggregation of IFN-Beta

Assessment of Percentage of Irreversible Aggregated Forms by Exclusion Chromatography in the Presence of Sodium Dodecyl Sulphate (SDS-SEC)

The percentage of irreversible aggregated forms of IFN-beta in the samples was determined by size exclusion chromatography. The chromatographic system consists of two columns connected in series (TSK-Gel G4000PWXL+TSK-Gel SuperAW400) and of a mobile phase containing a detergent, sodium dodecyl sulphate (SDS) (0.3% SDS-3.3 mM PBS buffer).

The irreversible aggregate content in the compositions is evaluated by comparison with a standard IFN-beta containing 1 to 1.5% of irreversible dimers. This standard consists of IFN-beta aggregated at 100° C. for 3.5 min diluted in a matrix which reproduces the sample. The standard and samples were diluted 20-fold in 2% SDS before analysis.

The chromatographic profile of each sample is compared to the profile of the standard aggregate material. Where irreversible aggregates in the sample to be treated are not detected or are below the standard, the aggregate content of the sample is given as being below 2%.

When irreversible aggregate content is above the standard, the quantification of aggregates is estimated through the quantification of the non-aggregated IFN-beta (monomer).

Percentage of Aggregated Forms by the Western Blot Method (WB)

The percentage of aggregated forms of IFN-beta in the samples was also assessed by Western blot. 100 ng of IFN-beta samples were diluted in Laemmli buffer at pH=6.8 (0.01% SDS, 62.4 mM Tris, 0.06% bromophenol blue, 10% glycerol) and deposited in wells of a 12% polyacrylamide gel. To quantify the rate of aggregates in the analyzed samples, a range of three standards of monomers of crude IFN-beta solution were deposited in different wells of the gel for each sample analysis. The three standards included 1 ng, 3 ng and 5 ng of IFN-beta per well, respectively corresponding to 1%, 3% and 5% compared with 100 ng of IFN-beta deposited for the samples. These standards were deposited after extemporaneous mixture of the crude solution of IFN-beta with the polymer P1 in the same ratio as IFN-beta and polymer P1 compositions of the invention to be analyzed.

In a first phase, the samples were separated by polyacrylamide gel electrophoresis in the presence of SDS (SDS-PAGE).

In a second phase, after migration of the grafted poly(glutamic acid) polymer, the IFN-beta and the aggregates in the gel, they were separated and transferred onto a nitrocellulose membrane. The IFN-beta was then specifically revealed using a primary anti-IFN-beta antibody, followed by a secondary antibody coupled to alkaline phosphatase. The membrane was then stained by a mixture of 5-bromo-4-chloro-3'-indolyphosphate p-toluidine (BCIP) and nitro blue tetrazolium chloride (NBT) where IFN-beta was detected by antibodies.

After staining, the ratio of aggregates in the tested compositions was determined by visually comparing the intensities of the standard bands and of a possible aggregate band.

The results obtained are given in Table 3:

TABLE 3

| Parameters of the compositions of Examples 2 and 4 of the invention | | |
| --- | --- | --- |
| Assessment of aggregated forms of IFN-beta | Example 2 | Example 4 |
| % of aggregated forms (WB) | not measured | <1 |
| % of aggregated forms (SEC-SDS) | <2 | <2 |

Experiment 4

Assessment of Aggregation of IFN-Beta in a Composition of the Invention

A liquid aqueous composition was prepared as described in Example 2, containing about 0.5 mg/mL IFN-beta and 22 mg/mL of grafted poly(glutamic acid) polymer.

The aggregate content of the aqueous composition was compared to that of a 0.4 mg/mL IFN-beta reference solution which did not contain grafted poly(glutamic acid) polymer.

0.7 mL of each of the compositions tested were placed in 3-mL vials and the solutions were heated for 30 min at 90° C.

i) Size Exclusion Chromatography

After heating, each composition was analyzed by size exclusion chromatography in the presence of SDS as described in Experiment 3. The peak corresponding to unmodified IFN-beta (monomer) was calculated from a range of IFN-beta standards encompassing the concentration described.

The results obtained are given in Table 4:

TABLE 4

| Assessment of aggregation | | |
| --- | --- | --- |
| | IFN-beta monomer peak before heating (%) | IFN-beta monomer peak after 30 min heating (%) |
| Solution of the invention | 100 | 108 |
| Reference solution | 100 | 44 |

These results clearly show that 100% of the IFN-beta was eluted as monomeric IFN-beta in the heated composition of the invention, while only 44% remained in the control solution.

ii) Western Blot

The presence or absence of aggregates of IFN-beta in the samples was also evaluated by Western blot (method described in Experiment 3).

Analysis of the membrane after staining reveals the presence of aggregates in the reference solution (not according to the invention), heated 30 min at 90° C., and further reveals a decrease in the amount of monomer relative to the unheated sample of reference solution. Instead, for the heated sample of the composition of the formulation according to the invention, no aggregate was detected, and the amount of monomer was identical to that of the sample of an unheated composition according to the invention.

This second method confirms the absence of aggregates in the composition of the invention.

In conclusion, the above tests clearly evidence that a composition of the invention prevents aggregation of IFN-beta.

Experiment 5

Stability of Freeze Dried Compositions of the Invention

Vials containing solid compositions of Examples 1 and 3 of the invention were placed in chambers maintained at 5° C. and 25° C.

Vials were taken out at different times, and reconstituted with water as described in Examples 2 and 4. Liquid compositions were analyzed using the methods described in the above experiments and results are presented in Tables 5 and 6.

TABLE 5

| Stability of the compositions of Examples 1 and 3 maintained at 5° C. | | | |
| --- | --- | --- | --- |
| Analysis | Time | Example 1 | Example 3 |
| $C_{IFN-beta}$ in mg/mL | T = 0 | 0.51 | 0.50 |
| | 1 month | 0.49 | 0.51 |
| | 2 months | 0.50 | not measured |
| | 3 months | 0.53 | 0.50 |
| | 6 months | 0.51 | 0.52 |

TABLE 5-continued

Stability of the compositions of Examples 1 and 3 maintained at 5° C.

| Analysis | Time | Example 1 | Example 3 |
|---|---|---|---|
|  | 9 months | 0.52 | 0.48 |
|  | 12 months | 0.50 | 0.49 |
|  | 18 months | 0.54 | 0.53 |
|  | 24 months | 0.53 | not measured |
| $C_{Pol}$ in mg/mL | T = 0 | 22 | 22 |
|  | 1 month | 21 | not measured |
|  | 2 months | 21 | not measured |
|  | 3 months | 23 | 22 |
|  | 6 months | 22 | 22 |
|  | 9 months | 22 | 22 |
|  | 12 months | 21 | 22 |
|  | 18 months | 22 | 22 |
|  | 24 months | 22 | not measured |
| pH | T = 0 | 6.9 | 6.9 |
|  | 1 month | 7.0 | 7.0 |
|  | 2 months | 6.9 | not measured |
|  | 3 months | 6.9 | 6.9 |
|  | 6 months | 6.9 | 6.9 |
|  | 9 months | 6.8 | 6.9 |
|  | 12 months | 7.0 | 7.0 |
|  | 18 months | 6.9 | 6.9 |
|  | 24 months | 6.8 | not measured |
| Osmolality in mOsm/kg | T = 0 | 318 | 308 |
|  | 1 month | 319 | 307 |
|  | 2 months | 281 | not measured |
|  | 3 months | 311 | 306 |
|  | 6 months | 300 | 308 |
|  | 9 months | 296 | 294 |
|  | 12 months | 306 | 300 |
|  | 18 months | 305 | 306 |
|  | 24 months | 305 | not measured |
| Antiviral activity in MIU/mL (% recovery) | T = 0 | not measured | 129.8 (101) |
|  | 1 month | not measured | 121.9 (95) |
|  | 2 months | not measured | not measured |
|  | 3 months | not measured | 125.6 (98) |
|  | 6 months | not measured | 134.3 (105) |
|  | 9 months | not measured | 123.6 (97) |
|  | 12 months | 125.4 (96) | 131 (102) |
|  | 18 months | not measured | 136.6 (107) |
|  | 24 months | 137.6 (106) | not measured |
| % aggregated forms (WB) | T = 0 | not measured | <1 |
|  | 1 month | not measured | <1 |
|  | 2 months | not measured | not measured |
|  | 3 months | not measured | <1 |
|  | 6 months | <1 | <1 |
|  | 9 months | <1 | <1 |
|  | 12 months | <1 | <1 |
|  | 18 months | ≤1 | <1 |
|  | 24 months | ≤1 | not measured |
| % aggregated forms (SEC-SDS) | T = 0 | <2 | <2 |
|  | 1 month | <2 | <2 |
|  | 2 months | <2 | not measured |
|  | 3 months | <2 | <2 |
|  | 6 months | <2 | <2 |
|  | 9 months | <2 | <2 |
|  | 12 months | <2 | <2 |
|  | 18 months | <2 | <2 |
|  | 24 months | <2 | not measured |
| Particle Size in nm | T = 0 | 18 | 17 |
|  | 1 month | 17 | 18 |
|  | 3 months | 19 | 17 |
|  | 6 months | 18 | 17 |
|  | 9 months | 18 | 18 |
|  | 12 months | 18 | 18 |
|  | 18 months | 18 | 17 |
|  | 24 months | 18 | not measured |

TABLE 6

Stability of the compositions of Examples 1 and 3 maintained at 25° C.

| Analysis | Time | Example 1 | Example 3 |
|---|---|---|---|
| $C_{IFN-beta}$ in mg/mL | T = 0 | 0.51 | 0.50 |
|  | 1 month | 0.48 | 0.51 |
|  | 2 months | 0.48 | 0.50 |
|  | 3 months | 0.53 | 0.50 |
|  | 6 months | 0.53 | 0.51 |
| $C_{Pol}$ in mg/mL | T = 0 | 22 | 22 |
|  | 1 month | 22 | 22 |
|  | 2 months | 22 | 22 |
|  | 3 months | 22 | 22 |
|  | 6 months | 22 | 22 |
| pH | T = 0 | 6.9 | 6.9 |
|  | 1 month | 6.9 | 7.0 |
|  | 2 months | 6.9 | 6.9 |
|  | 3 months | 6.9 | 6.9 |
|  | 6 months | 6.9 | 6.9 |
| Osmolality in mOsm/kg | T = 0 | 318 | 308 |
|  | 1 month | 333 | 305 |
|  | 2 months | 316 | 310 |
|  | 3 months | 324 | 307 |
|  | 6 months | 312 | 299 |
| Antiviral activity in MIU/mL (% recovery) | T = 0 | not measured | 129.8 (101) |
|  | 1 month | not measured | 130.1 (102) |
|  | 2 months | not measured | 130.0 (102) |
|  | 3 months | 121.5 (93) | 123.6 (97) |
|  | 6 months | not measured | 124.7 (97) |
| % aggregated forms (WB) | T = 0 | not measured | <1 |
|  | 1 month | not measured | <1 |
|  | 2 months | not measured | <1 |
|  | 3 months | not measured | <1 |
|  | 6 months | <1 | <1 |
| % aggregated forms (SEC-SDS) | T = 0 | <2 | <2 |
|  | 1 month | <2 | <2 |
|  | 2 months | <2 | <2 |
|  | 3 months | <2 | <2 |
|  | 6 months | <2 | <2 |
| Particle Size in nm | T = 0 | 18 | 17 |
|  | 1 month | 19 | 18 |
|  | 2 months | 19 | 18 |
|  | 3 months | 18 | 19 |
|  | 6 months | 17 | 18 |

The above values clearly evidence that the freeze-dried compositions of the invention are stable over a period of at least 24 months at 5° C. and at least 6 months at 25° C. In particular, they are stable vis-à-vis IFN-beta aggregation as shown by the percentage of IFN-beta monomer remaining above 98% over the same period, whereas the bioactivity of the antiviral IFN-beta thus formulated is not changed.

Experiment 6

Pharmacokinetics of Compositions According to the Invention in Cynomolgus Monkeys A liquid composition F prepared as described in Example 2 and an immediate-release commercial formulation (IRCF) were tested.

Both compositions were administered subcutaneously at a dose of 84 mg/kg in a volume of 0.17 mL/kg to 24 monkeys divided into 6 groups.

The results obtained are given in Table 7:

TABLE 7

Compared pharmacokinetics

| Composition | Cmax (pg/mL) | Tmax (h) | AUC 0-t (ng · h/mL) | T > LID (h) | RBA (%) |
|---|---|---|---|---|---|
| IRCF | 1155 | 0.75 | 14.6 | 51 | 100 |
| Composition F | 2199 | 48 | 91.5 | 122 | 52 |

RBA: Relative bioavailability compared to immediate-release form
Cmax: maximum plasma concentration.
Tmax: Time when plasma concentration is maximum.
AUC: Area under the curve.
T > LID (lower limit of detection): Duration during which the active ingredient is detectable.

The bioavailability of IFN-beta in the liquid composition F was 52% of that of the immediate-release composition. IFN-beta was far longer detectable in the liquid composition F than in the immediate release composition.

As shown in FIG. 1, the plasmatic profile of IFN-beta released from the liquid composition F stretches over a period of at least 120 hrs. This formulation allows a weekly administration to patients.

Experiment 7

Characterization of the In-Vitro Release Profile of the Compositions According to the Invention in Comparison to a Composition Out of the Scope of the Invention Using the T1 Test Liquid compositions were prepared as described in Examples 2 and 4 and further tested using the T1 test. For each liquid composition the in-vitro test was repeated 6 times. A liquid solution out of the scope of the invention, namely comprising 0.5 mg/mL of IFN-beta only and obtained by simple dissolution of the IFN-beta solution, was prepared in a 50 mM sodium acetate buffer for comparison. The IFN-beta solution out of the scope of the invention was tested 3 times with the same T1 test.

Results:

The cumulated IFN-beta amount released for each tested composition is given in Table 8:

TABLE 8

Cumulated amount of IFN-beta released from compositions as a function of time (% IFN-beta released versus initial IFN-beta quantity injected in the in-vitro test - mean of 6 or 3 assays)

| Compositions Time (hrs) | 0.5 mg/mL IFN-beta solution without grafted poly(glutamic acid) polymer (%) | Liquid composition from Example 2 according to the invention (%) | Liquid composition from Example 4 according to the invention (%) |
|---|---|---|---|
| 0.03 | 0.3 | not measured | not measured |
| 0.10 | 31.4 | not measured | not measured |
| 0.13 | 52.1 | not measured | not measured |
| 0.17 | 61.7 | not measured | not measured |
| 0.20 | 73.6 | not measured | not measured |
| 0.27 | 88.1 | not measured | not measured |
| 0.30 | 91.8 | not measured | not measured |
| 0.33 | 94.3 | not measured | not measured |
| 0.37 | 95.7 | not measured | not measured |
| 0.40 | 96.9 | not measured | not measured |
| 0.47 | 98.4 | not measured | not measured |
| 0.50 | not measured | 2.7 | 4.7 |
| 0.60 | 100 | not measured | not measured |
| 1 | — | 12.3 | 15.8 |
| 1.5 | — | 20.5 | 25.2 |
| 2 | — | 27.7 | 33.2 |
| 2.5 | — | 34.7 | 40.8 |
| 3 | — | 41.7 | 47.8 |
| 3.5 | — | 48.6 | 54.6 |
| 4 | — | 55.3 | 61.0 |
| 4.5 | — | 62.0 | 67.2 |
| 5 | — | 68.0 | 73.0 |
| 5.5 | — | 73.8 | 78.3 |
| 6 | — | 79.3 | 83.1 |
| 7 | — | 87.9 | 90.3 |
| 8 | — | 93.0 | 95.7 |
| 9 | — | 95.8 | 98.5 |
| 12 | — | 99.9 | 99.9 |
| 16 | — | 100.0 | 100.0 |
| 22 | — | 100.0 | 100.0 |

IFN-beta was released at a level of 50% in a few minutes from the IFN-beta solution without grafted poly(glutamic acid) polymer whereas the same amount was released from the liquid compositions according to the invention after more than 2 hrs.

The IFN-beta release was much prolonged in a composition of the invention compared to an IFN-beta solution.

Experiment 8

Characterization of the In-Vitro Release Profile of a Composition According to the Invention in Comparison to Compositions Out of the Scope of the Invention Using the T2 Test Liquid compositions were prepared as described in Examples 8 and 10 and further tested using the T2 test. For each liquid composition the in-vitro test was repeated 3 times.

Results:

The cumulated IFN-beta amount released for each tested composition is given in Table 9:

TABLE 9

Cumulated amount of IFN-beta released from compositions as a function of time (% IFN-beta released versus initial IFN-beta quantity injected in the in-vitro test - average of 3 assays)

| Compositions Time (hrs) | Liquid composition from Example 8 according to the invention (%) | Liquid composition from Example 10 out of the scope of the invention (%) |
|---|---|---|
| 0.50 | 5.6 | 27.5 |
| 1 | 24.2 | 82.6 |
| 1.5 | 51.2 | 96.9 |
| 2 | 66.9 | 98.1 |
| 2.5 | 79.3 | 98.3 |
| 3 | 88.5 | 98.3 |
| 3.5 | 94.8 | 98.4 |
| 4 | 97.5 | 98.4 |
| 4.5 | 98.8 | 98.4 |
| 5.5 | 98.9 | 98.5 |
| 7.5 | 99.3 | 98.5 |
| 11.5 | 100.0 | 99.7 |
| 15 | 100.0 | 100.0 |

IFN-beta was released at a level of 60% in less than 1 h from the liquid composition out of the scope of the invention (Example 10) whereas the same amount was released from the liquid compositions according to the invention after more than 1.5 hrs (Example 8).

The IFN-beta release was much prolonged in a composition of the invention compared to the liquid compositions out of the scope of the invention.

REFERENCES

1. Derynk R. et al., Nature 1980; 285, 542-547.
2. Familletti, P. C., Rubinstein, S., and Pestka, S. 1981 "A Convenient and Rapid Cytopathic Effect Inhibition Assay for Interferon," in Methods in Enzymology, Vol. 78 (S. Pestka, ed.), Academic Press, New York, 387-394.
3. Mark D. F. et al., Proc. Natl. Acad. Sci. U.S.A., 81 (18) 5662-5666 (1984).
4. Pestka, S. (1986) "Interferon Standards and General Abbreviations, in Methods in Enzymology (S. Pestka, ed.), Academic Press, New York 119, 14-23.
5. Rubinstein, S., Familletti, P. C., and Pestka, S. Convenient Assay for Interferons. J. Virol 1981; 37, 755-758.
6. Shepard H. M. et al., Nature 1981; 294, 563-565.

What is claimed is:

1. A solid pharmaceutical composition comprising:
   interferon-beta (IFN-beta);
   a grafted poly(glutamic acid) polymer having an average molecular weight between 26,000 and 40,000 g/mol, grafted with alpha-tocopherol substituents, the average molar grafting ratio being 4.5-5.5 moles %, wherein the weight/weight ratio between said grafted poly(glutamic acid) polymer and IFN-beta is between 24 and 125: and
   a sucrose in a sucrose/IFN-beta weight/weight ratio between 100 and 600.

2. The composition according to claim 1, wherein the average molar grafting ratio of alpha-tocopherol substituents is about 5%.

3. The composition according to claim 1, said composition further comprising an antioxidant in an antioxidant/IFN-beta weight/weight ratio between 2 and 7.

4. The composition according to claim 1, said composition comprising:
   interferon-beta (IFN-beta);
   a grafted (glutamic acid) polymer having an average molecular weight between 26,000 and 40,000 g/mol, grafted with alpha-tocopherol substituents, the average molar grafting ratio being 4.5-5.5 moles %, wherein the weight/weight ratio between said grafted poly(glutamic acid) polymer and IFN-beta is between 24 and 125;
   methionine in a methionine/1FN-beta weight/weight ratio between 2 and 7; and
   sucrose in a sucrose/IFN-beta weight/weight ratio between 100 and 600.

5. The composition according to claim 1, said composition comprising:
   a) about 0.5 mg IFN-beta;
   b) about 22 mg of grafted poly(glutamic acid) polymer having an average molecular weight between 26,000 and 40,000 g/mol, grafted with alpha-tocopherol substituents, the average molar grafting ratio being 4.5-5.5 moles %;
   c) about 1.5 mg methionine; and
   d) about 76 mg sucrose;
   or a multiple or sub-multiple of said amounts.

6. The composition according to claim 1, wherein said composition is a lyophilisate.

7. A liquid aqueous composition comprising the solid pharmaceutical composition according to claim 1 dissolved in a solvent.

8. The liquid composition according to claim 7, wherein the concentration of IFN-beta is between 0.2 and 0.8 mg/mL.

9. The liquid composition according to claim 7, wherein the concentration of grafted poly(glutamic acid) polymer is from 19 to 25 mg/mL.

10. The liquid composition according to claim 7, said composition comprising:
    a) about 0.5 mg/ml IFN-beta;
    b) about 22 mg/ml of poly(glutamic acid) polymer having an average molecular weight between 26,000 and 40,000 g/mol, grafted with alpha-tocopherol substituents, the average molar grafting ratio being 4.5-5.5 moles %;
    c) about 1.5 mg/ml methionine; and
    d) about 76 mg/ml sucrose.

* * * * *

UNITED STATES PATENT AND TRADEMARK OFFICE
CERTIFICATE OF CORRECTION

PATENT NO.        : 9,272,020 B2
APPLICATION NO.   : 14/118757
DATED             : March 1, 2016
INVENTOR(S)       : Leblanc et al.

Page 1 of 1

It is certified that error appears in the above-identified patent and that said Letters Patent is hereby corrected as shown below:

In the Specification
Column 1,
Line 32, "interferon-gamma Further" should read --interferon-gamma. Further--.

Column 9,
Line 33, "Considering $M_1$ is considered the" should read --$M_1$ is considered the--.

Column 10,
Lines 2-3, "PEARLITOL, SD200" should read --PEARLITOL SD200--.
Lines 62-63, "(d) sterilizing at least once the resulting mixture at least once; and" should read --(d) sterilizing the resulting mixture at least once; and--.

Column 16,
Line 51, "gently stiffed" should read --gently stirred--.
Line 67, "4.76 mm" should read --4.76 mm.--.

Column 17,
Line 13, "stiffed manually" should read --stirred manually--.
Line 26, "4.76 mm" should read --4.76 mm.--.
Line 53, "4.76 mm" should read --4.76 mm.--.

Column 18,
Line 51, "4.76 mm" should read --4.76 mm.--.

In the Claims
Column 27,
Line 32, "125: and" should read --125; and--.

Column 28,
Line 8, "methionine/1FN-beta" should read --methionine/IFN-beta--.

Signed and Sealed this
Fourteenth Day of June, 2016

Michelle K. Lee
*Director of the United States Patent and Trademark Office*